US009833170B2

(12) United States Patent
Mair et al.

(10) Patent No.: US 9,833,170 B2
(45) Date of Patent: Dec. 5, 2017

(54) IMAGING OF INTELLIGENT MAGNETIC PARTICLES

(71) Applicant: WEINBERG MEDICAL PHYSICS LLC, Bethesda, MD (US)

(72) Inventors: Lamar Odell Mair, Washington, DC (US); Aleksandar Nelson Nacev, Bethesda, MD (US); Irving N. Weinberg, Bethesda, MD (US)

(73) Assignee: Weinberg Medical Physics Inc., North Bethesda, MD (US)

( * ) Notice: Subject to any disclaimer, the term of this patent is extended or adjusted under 35 U.S.C. 154(b) by 18 days.

(21) Appl. No.: 14/574,020

(22) Filed: Dec. 17, 2014

(65) Prior Publication Data

US 2015/0164365 A1 Jun. 18, 2015

Related U.S. Application Data

(60) Provisional application No. 61/917,146, filed on Dec. 17, 2013.

(51) Int. Cl.
*A61B 5/00* (2006.01)
*A61B 5/07* (2006.01)
*A61B 5/05* (2006.01)

(52) U.S. Cl.
CPC ............ *A61B 5/073* (2013.01); *A61B 5/0515* (2013.01)

(58) Field of Classification Search
CPC ........ A61B 5/05; A61B 5/6846; A61B 5/0002
See application file for complete search history.

(56) References Cited

U.S. PATENT DOCUMENTS

| 5,578,814 | A * | 11/1996 | Dadali | ............... H01L 27/14665 250/208.1 |
|---|---|---|---|---|
| 2005/0118494 | A1 | 6/2005 | Choi | |
| 2006/0152309 | A1 | 7/2006 | Mintchev et al. | |
| 2007/0216991 | A1 | 9/2007 | Edamatsu et al. | |
| 2009/0131738 | A1 | 5/2009 | Farren et al. | |
| 2012/0035540 | A1 | 2/2012 | Ferren et al. | |

OTHER PUBLICATIONS

Notification Of Transmittal of The International Search Report And The Written Opinion of the International Search Authority for International Patent Application No. PCT/US2014/070943, dated Dec. 17, 2014.

* cited by examiner

*Primary Examiner* — Joseph M Santos Rodriguez
(74) *Attorney, Agent, or Firm* — Barnes & Thornburg LLP

(57) ABSTRACT

An apparatus and method apply magnetic fields by generators external to a body or body part with sensors within an in vivo source that are sensitive to applied magnetic fields Through the use of these applied magnetic fields and sensitive sensors, disclosed embodiments can realize much better spatial resolution than is conventionally possible.

30 Claims, 1 Drawing Sheet

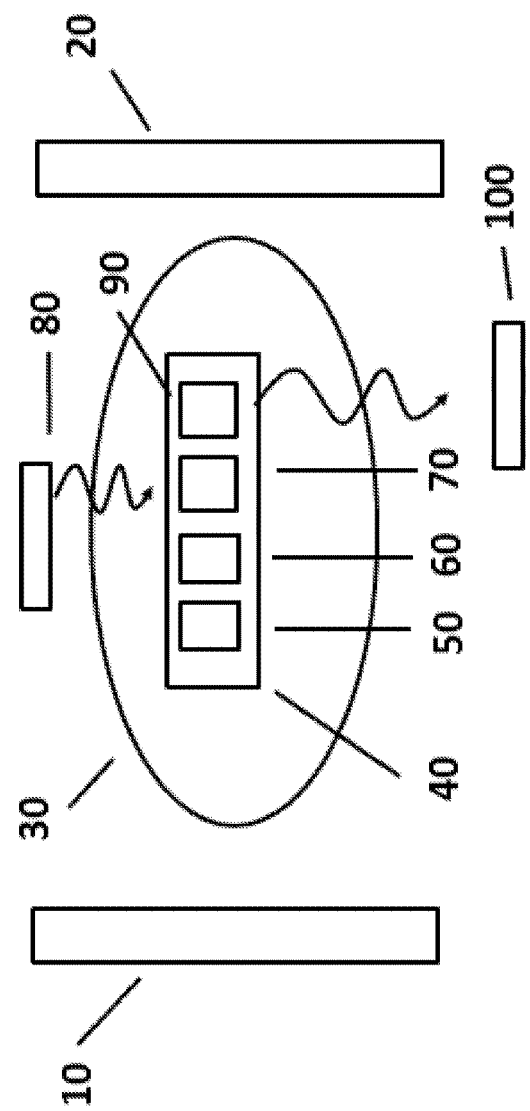

IMAGING OF INTELLIGENT MAGNETIC PARTICLES

CROSS REFERENCE

This application claims priority under 35 U.S.C. 119(e) U.S. Provisional Patent Application 61/917,146 by I. N. Weinberg et al. (incorporated by reference in its entirety) on Dec. 17, 2013, entitled "Intelligent Magnetic Particle Imaging."

FIELD OF THE INVENTION

Disclosed embodiments are directed to high-resolution functional imaging in a body, or body part, in particular using magnetic imaging and particle imaging instruments.

SUMMARY

Disclosed embodiments utilize application of magnetic fields by generators external to the body or body part and by one or more miniature electronic circuits internal to the body or body part, where the operation of (and/or transmission of information from) said miniature electronic circuits is affected by the applied magnetic fields. Through the use of these applied magnetic fields and miniature electronic circuits, disclosed embodiments can realize much better spatial resolution than is conventionally possible.

Disclosed embodiments utilize one or more magnets or electromagnets or antennae that impose electrical and/or magnetic spatially-variant gradients upon a part of a body or body part, one or more miniature electronic circuits (located inside the body part), and a receiver of energy emanating from the one or more miniature electronic circuits, where the receiver is located outside the body part.

In accordance with at least one disclosed embodiment, the one or more miniature electronic circuits contain (or are connected to) a transmitter of radio frequency (RF) and/or sonic energy for the purpose of communication from (and/or powering of) the one or more miniature electronic circuits.

It is understood that the miniature electronic circuit may be a single particle, for example a particle having spintronic or plasmonic features that provide the desired function, or the miniature electronic circuit may be a composite of several components.

In accordance with at least one disclosed embodiment, the receiver is for sensing the RF and/or sonic energy emitted by the one or more miniature electronic circuits.

BRIEF DESCRIPTION OF THE FIGURES

The detailed description particularly refers to the accompanying figures in which FIG. 1 which illustrates an embodiment of the apparatus for imaging performed in accordance with the disclosed embodiments.

DETAILED DESCRIPTION

Disclosed embodiments utilize application of magnetic fields by generators external to the body or body part and by one or more miniature electronic circuits internal to the body or body part, where the operation of (and/or transmission of information from) said miniature electronic circuits is affected by the applied magnetic fields. Through the use of these applied magnetic fields and miniature electronic circuits, disclosed embodiments can realize much better spatial resolution than is conventionally possible.

Additionally, in accordance with at least one embodiment, a multiplicity of microscopic in vivo sources may be used to collect position information.

The present invention relies in part on the previously filed application "Method and Apparatus for High Resolution Physiological Imaging of Neurons", filed on May 18, 2013 as application Ser. No. 13/903,137, and on patent applications and awarded patents included by reference.

Elements of an embodiment of the invention are:
one or more magnets or electromagnets or antennae that impose electrical and/or magnetic spatially-variant gradients upon a part of a body or body part;
one or more miniature electronic circuits (located inside the body part), said circuits containing (or connected to) a transmitter of radiofrequency (RF) and/or sonic energy for the purpose of communication from (and/or powering of) the one or more miniature electronic circuits; and
a receiver of energy (located outside the body part) for sensing the RF and/or sonic energy emitted by the one or more miniature electronic circuits.

It is understood that the term transmitter of RF energy also includes the possibility of reflection of energy that has emanated from a source outside the body part and is then re-emitted from the miniature electronic circuit to a receiver outside the body part.

In accordance with at least one embodiment, the one or more miniature electronic circuits sense the local milieu in the body or body part(for example, by sensing magnetic field, voltage, current, chemical substances, receptors, temperature, and/or pressure, etc.).

It is understood that the term "miniature electronic circuit" includes the possibility that some or all of the components of the circuit operate through the circulation of particles other than electrons, for example photons, phonons, and/or hole charge carriers. It is also understood that the miniature electronic circuit may include some computational capability.

In accordance with at least one embodiment, the miniature electronic circuit is less than 10 microns in size of the smallest dimension. In accordance with at least one embodiment, the miniature electronic circuit is capable of crossing the blood brain barrier as a result of a coating or as a result of externally propulsive magnetic fields (see, for example, the publication by I. N. Weinberg et al. in 2012, entitled "Non-invasive Image-Guided Brain Access with Gradient Propulsion of Magnetic Nanoparticles", in the Conference Proceedings of the IEEE Nuclear Symposium and Medical Imaging Conference, pages 3732-3734, incorporated herein by reference in its entirety).

In accordance with at least one embodiment, the electromagnets that impose electrical and/or magnetic spatially-variant gradients upon the body may be configured, posited or controlled to create very high magnetic fields, for example by using pulsed power techniques and cooled conductors (see for example, the publication by M. Yu et al, entitled "A 670 GHz gyrotron with record power and efficiency", published in 2012 in the journal Applied Physics Letters, vol. 101(15), pages 153503, incorporated herein by reference in its entirety).

In operation, disclosed embodiments of the invention describe the strength and/or direction of the electrical field at locations in the body. One or more miniature electronic circuits are introduced into the body or body part. The introduction may occur by intravenous injection, injection into the cerebrospinal fluid, ingestion, or some other means.

The one or more circuits may include at least one sensor of electric field strength (and/or field direction) and/or at least one sensor of magnetic field strength (and/or direction) and/or a sensor of chemical qualities of the local milieu (for example pH). As an example, the at least one electric sensor may be a voltage-controlled oscillator that can sample the local electric field. The at least one magnetic sensor may be a cantilever which creates an electrical voltage that is dependent on the amplitude and/or direction of the magnetic field, for example through deformation and/or compression of a piezoelectric material, as taught by T-D Onuta et al, in a 2011 publication entitled "Energy harvesting properties of all-thin-film multiferroid cantilevers", published in Applied Physics Letters, volume 99, page 203506., incorporated herein by reference in its entirety.

Alternatively, the magnetic sensor may be a cantilever with or without magnetizable sections so that the sensor acts as a switch with respect to electrical conductance.

Electromagnets external to the body may impose a magnetic gradient on the body or body part, such that a specific region of the body or body part has a specific magnetic field value present at the location that is to be sampled with the at least one miniature electronic circuit. In accordance with at least one embodiment, the at least one magnetic sensor on or in the one miniature electronic circuit creates a voltage based on the magnetic field extant at the location of the at least one miniature electronic circuit, thereby registering the location of the miniature electronic circuit in the body or body part. The miniature electronic circuit emanates a signal that is received by one or more sensors located external to the body or body part. The emanated signal may be RF, or may be ultrasonic in nature.

In accordance with at least one embodiment, the externally-applied magnetic field may power the miniature electronic circuit, for example through the compression of a piezoelectric element as in the above-cited publication by T-D Onuta et al. The externally-applied magnetic field may change in time, so as to power the miniature electronic circuit through inductive coupling, as in the publication by A. Denisov and E. Yeatman entitled "Ultrasonic vs. Inductive Power Delivery for Miniature Biomedical Implants", published in the conference proceedings of the 2010 IEEE International Conference on Body Sensor Networks, pages 84-89, incorporated herein by reference in its entirety.

In an alternative embodiment, the miniature electronic circuit may be powered through ultrasound applied to the body or body part, as in the publication by A. Denisov.

In another alternative embodiment, the miniature electronic circuit may be powered by a particulate fuel cell. For example, glucose fuel cells have been proposed as useful devices for powering electronics inside the bodies of humans and other animals. Several groups have performed experiments demonstrating the application of implantable glucose fuel cells in various animals, including dogs, sheep, rats snails, lobsters, and cockroaches. Some of these examples are reviewed in the publication "Towards glucose biofuel cells implanted in the human body for powering artificial organs: Review", by Serge Cosnier, Alan Le Goff, and Michael Holzinger, in Electrochemistry Communications, Volume 38, pages 19-23, 2014, incorporated herein by reference in its entirety.

The primary functioning processes of an implantable glucose fuel cell may rely on the oxidation of glucose at an anode, and the reduction of oxygen at a cathode. Connecting the anode and cathode surfaces across a resistive load allows for the flow of electrons, which can power a device. A particulate fuel cell that can reside in a human or animal body or cell, wherein the fuel cell is self-contained and has an anode, a cathode, a separator membrane, and a magnetic component. In various implementations, the fuel cell may include segments for the oxidation of a biofuel (such as glucose) and the reduction of oxygen. For example such fuel cells may be made using technology disclosed in U.S. Provisional Patent Application No. 62/068,083, filed Oct. 24, 2014 and entitled "Scalable, Massively Parallel Process for Making Micro-Scale Particles that Incorporate a Fuel Cell" hereby incorporated by reference in its entirety.

In accordance with at least one embodiment, the one or more miniature electronic circuit may sample its local milieu (for example, monitoring voltage with one or more antenna structures) and modulate the signal transmitted to a receiver outside the body or body part (for example, by using a voltage controlled oscillator and/or through a digitally-encoded modulation).

The signal received by the external receiver may be analyzed by a computer to determine the location of the at least one miniature electronic circuit in the body or body part, and the modulation of the signal related to the local milieu samples by the miniature electronic circuit. It should be understood that additional examinations (for example, Magnetic Resonance Imaging (MRI) may be interleaved or precede or follow the reception of signal in order to provide an anatomic or physiological reference to assist in interpreting the significance of the signals received by the external receiver.

Through such analysis, an image can be formed of the location of the at least one miniature electronic circuit by altering the spatial configuration of the magnetic gradient which is applied to the body or body part and recording the signals received by the receiver external to the body or body part. The image can represent properties of the body or body part by analyzing the signals received by the receiver external to the body or body part, since these signals were influenced by the those local properties as experienced by the at least one miniature circuit.

In one way, the above embodiment can be conceptually thought of as the invention of an artificial particle with an artificial "gyromagnetic ratio," which may be used to localize one or more such particles through the application of one or more externally-applied magnetic gradient(s), for example, those used in magnetic resonance imaging.

Unlike the naturally-occurring protons that are interrogated with MRI, the artificial particle's response to the externally-applied magnetic gradient(s) may be optimized through selection of appropriate internal components and connections within the at least one miniature electronic circuit.

It is understood that the mode of operation of the at least one miniature electronic circuit may be programmed through the application of externally-applied electromagnetic fields before and/or after insertion of the at least one miniature electronic circuit into the body or body part.

It is understood that many of the techniques used in MRI may similarly be applied to this invention. For example, phase encoding may be implemented through the use of memory within the at least one miniature electronic circuit. The memory could be implemented digitally or through analog means (for example with a capacitor that stored charge).

Although most of this disclosure described the operation of a miniature electronic circuit, it is understood that the concept may be generalized to include at least one mechanical mechanism in which a miniaturized structure (for example a tuning fork) may have its functionality varied as a result of the magnetic field in which it resides (for example, as a result of having magnetizable materials on one arm of a resonant structure), and this miniaturized structure's location and/or milieu sensed via an external sensor. For example, the miniaturized structure could emit sounds that would be picked up by an external sensor, or could resonate in response to a sonic or ultrasonic beam created by an external device.

It is understood that the term "outside the body or body part" as applied to a component includes the case where part of the component is on or in the body or body part, and that part communicates with another component that is outside the body or body part. For example, an antenna may be placed in a body or body part orifice to receive signals from the at least one miniature electronic component, and that antenna may be connected with or without a wire to another antenna that is outside the body or body part.

In accordance with at least one embodiment, when the magnetic field value is below a threshold to which the at least one magnetic sensor is sensitive, the at least one magnetic sensor (acting as a switch) registers that little or no magnetic field is present at the desired sampling location, thereby registering the location of the miniature electronic circuit in the body or body part.

In accordance with at least one embodiment, the sensor may switch on or off depending on the combination of magnetic field values in one or more dimensions, thereby registering the location of the miniature electronic circuit in the body or body part.

In accordance with at least one embodiment, a sensor within the miniature electronic circuit may include dielectric materials that rotate, deform, activate, or translate in the presence of electric fields and whose such changes thereby measure the magnitude and/or direction of said electric fields. Such changes would include what is commonly termed a capacitative probe measurement.

In accordance with at least one embodiment, a sensor within the miniature electronic circuit may include magneto-electric and/or piezoelectric materials that create a voltage or current in the presence of magnetic fields and which voltage thereby encodes the magnitude and/or direction of the magnitude fields. In an embodiment, a sensor within the miniature electronic circuit may include piezoelectric materials that create electrical current in the presence of ultrasound and this electrical current generates magnetic fields that encode information from the sensor (such as location, state, or other properties being measured by the sensor).

In accordance with at least one embodiment, a part of the one or more antenna structures connected to the miniature electronic circuit may contact or pierce the membrane of a cell, in order to measure trans-membrane potential. It is known that trans-membrane potentials may be very high, for example as taught in the MIT Technology Review article written by Katherine Bourzac on Dec. 10, 2007, and entitled "Lightning Bolts within Cells," herein incorporated by reference in its entirety.

In accordance with at least one embodiment, a sensor connected to the miniature electronic circuit and which is sampling the local milieu may be sensitive to the presence of chemicals or chemical properties (for example, pH).

In accordance with at least one embodiment, the magnetic sensor detecting the presence and magnitude of the magnetic gradient may be used to sense local currents generated in the body or body part by cells or organs, e.g., the cells are neurons in the brain.

In accordance with at least one embodiment, the signal transmitted by the one or more miniature electronic circuit is at a frequency, or at a time, that is different than any signals received by the miniature electronic circuit from an external source. In an alternative embodiment, the RF frequency emitted by the miniature electronic circuit is similar to the RF frequency emitted by the transmitter, and the two signals are separated through splitter techniques widely known in the MRI community (see for example U.S. Pat. No. 4,859,950, entitled "Balun circuit for radiofrequency coils in magnetic resonance systems accordance with at least one," incorporated by reference in its entirety).

In accordance with at least one embodiment the signal transmitted by the one or more miniature electronic circuit is at a frequency to which the external RF receiver is tuned.

In an alternative embodiment, the miniature circuit may emit electromagnetic radiation that is detected by a sensor of magnetic fields that is located outside the body or body part, for example a superconducting quantum interference device.

Utility of the presently disclosed embodiments relates to the spatial resolution realizable through use of the method and apparatus. Earlier inventions relating to magnetic particle imaging, such as Weizenecker et al (U.S. Pat. No. 8,355,771), relied on the interaction between the intrinsic magnetic properties of metallic particles and an externally-applied set of magnetic fields in order to localize the metallic particles. The spatial resolution of these prior inventions was limited (among other things) by the minimum magnetic field strength that was capable of saturating the metallic particles.

For most metallic particles, saturation occurs at a magnetic field strength on the order of hundreds of milliTeslas. Magnetic gradients cannot easily be applied by electromagnets with maximal strengths in excess of one Tesla.

In a typical human body or body part with maximal dimension of 0.5 meters, this leads to a maximal gradient strength on the order of 2 T/m (or 20 milliTeslas per 10 mm). Since the saturation strength of most magnetizable materials is more than 20 milliTeslas, a spatial resolution limit on the order of 10 mm is encountered.

The present invention, by contrast, solves this technical problem by providing a technical solution wherein a circuit magnetic field sensor that is sensitive to a much lower magnetic field than 10 milliTeslas is provided. For example, a flexural gate transistor may be employed to achieve nanotesla sensitivity, as in the publication by F. Lee et al, entitled "Magnetoelectric Flexural Gate Transistor with NanoTesla Sensitivity", published in 2013 in the Journal of Micromechanical Systems, Vol. 22, Issue 1, pages 71-79, incorporated by reference in its entirety.

With such a magnetic field sensor incorporated into the miniature electrical circuit, the spatial resolution possible with a 1 Telsa maximal gradient strength applied over 0.5 meters (i.e., average gradient strength of 2 T/m) would be in the micron range, since placement of the miniature electric circuit in the location of the zero-crossing of the gradient field would be bound within a space corresponding to nanoTeslas.

Applying a stronger magnetic gradient (e.g., 10 T) would result in an even better spatial resolution. As shown by I. N. Weinberg et al in the issued U.S. Pat. No. 8,154,286 (incorporated by reference in its entirety), it is possible to apply very high magnetic pulsed fields to the body or body part without causing uncomfortable nerve stimulation if the rise- and fall-times are less than ten microseconds.

The term "intelligent magnetic particle imaging" in the present invention's disclosure is used to describe the orientation of the present approach. More specifically, unlike prior magnetic particle imaging approaches that employ pieces of iron, the sensors connected to, included in or utilized by the miniature electronic circuit are the elements which provide useful information to the user. Each of the miniature electronic circuits eventually provides information to the user as to its location ("where I am"), its activation ("look at me") and its milieu ("this is what I am feeling").

The disclosed embodiment may be compared to a prior invention describing the use of external electric fields to localize an in-vivo object, as taught by M. Frisch et al in U.S. Pat. No. 6,904,308, entitled "Array system and method for localizing an in vivo source," incorporated herein by reference in its entirety. In that prior invention, the in vivo source emanated radiation that was detected by a plurality of antenna elements external to the body or body part. Among other differentiating aspects, the prior invention by Frisch et al did not envision the application of magnetic fields by generators external to the body or body part, and did not envision sensors within the in vivo source that were sensitive to applied magnetic fields, as in the present invention.

The present invention, through the use of these applied magnetic fields and sensitive sensors, can realize much better spatial resolution than in the prior invention by Frisch et al.

Another differentiating point is that the present invention envisions a multiplicity of microscopic in vivo sources, while the prior invention by Frisch et al was intended for localization of a single in vivo source, and was not intended to be of use (and would not be effective) in collecting position information from multiple in vivo sources.

In accordance with at least one embodiment, the apparatus includes or utilizes means for delivering therapy locally, for example, with emanation of one or more electrical and/or acoustic pulses from the miniature electronic circuit.

In accordance with at least one embodiment, the miniature electronic circuit may be attached to a miniature chamber containing one or more medications, which may be released to treat a condition. The delivery may be dependent on the localization of the at least one miniature electronic circuit with the externally-imposed electromagnetic field and/or local sensor measurements and/or RF pulses received by at least one miniature electronic circuit from an external source.

Reference is made to FIG. 1, which describes an embodiment of the apparatus whose method and mode of operation is listed above. FIG. 1 includes gradient-generating coils 10 and 20 external to body or body part 30, which may generate magnetic gradients at the location of at least one miniature circuit 40 in a body part 30. Miniature electrical circuit 40 may include, as functional circuit elements, one or more magnetic sensors 50, and may include one or more sensors of the local milieu 60, an electromagnetic receiver 70 (receiving electromagnetic radiation from an external RF generator 80), and an electromagnetic transmitter 90 (transmitting electromagnetic radiation to an external RF receiver 100).

It should be understood that the gradient-generating coils are under the control of a controller that enables, automatic, semi-automatic and/or manual control of generated magnetic fields and magnetic gradients.

It is understood that the term radiation includes emission and reflection of RF energy, and also includes other methods of transmitting information over a distance, for example with entangled quantum effects.

It should be understood that control and cooperation of the components of the instrument may be provided using software instructions that may be stored in a tangible, non-transitory storage device such as a non-transitory computer readable storage device storing instructions which, when executed on one or more programmed processors, carry out he above-described method operations and resulting functionality. In this case, the term non-transitory is intended to preclude transmitted signals and propagating waves, but not storage devices that are erasable or dependent upon power sources to retain information.

Although not specifically illustrated, it should be understood that the components illustrated in FIG. 1 and their associated functionality may be implemented in conjunction with, or under the control of, one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments of the present invention. Such alternative storage devices should be considered equivalents.

While certain illustrative embodiments have been described, it is evident that many alternatives, modifications, permutations and variations will become apparent to those skilled in the art in light of the foregoing description. While illustrated embodiments have been outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

As a result, it will be apparent for those skilled in the art that the illustrative embodiments described are only examples and that various modifications can be made within the scope of the invention as defined in the appended claims.

We claim:

1. An apparatus for imaging a portion of a subject's brain, the apparatus comprising:
    at least one miniature electronic circuit that is less than 10 microns in size of a smallest dimension and being positioned in the subject's brain, the at least one miniature electronic circuit including a magneto-electric sensor that senses magnetic fields and encodes a magnitude and/or direction of the sensed magnetic fields and a transmitter of information from the miniature electronic circuit;

a receiver of the information, the receiver being located, at least in part, external to the subject's body; and a generator of spatially-variant magnetic gradient, wherein the generator is located, at least in part, external to the subject's body, wherein the at least one miniature electronic circuit sensor detects current or voltage generated by neurons in the subject's brain, and wherein, the at least one miniature electronic circuit transmits information to the external receiver in a manner that depends on the current or voltage detected by the magneto-electric sensor.

2. The apparatus of claim 1, wherein the magneto-electric sensor is within or otherwise attached to the at least one miniature electronic circuit, wherein output of the magneto-electric sensor is used by the at least one miniature electronic circuit to modulate information emitted by the at least one miniature electronic circuit.

3. The apparatus of claim 1, in which the information transmitted by the at least one miniature electronic circuit is mediated by emanation of electromagnetic radiation.

4. The apparatus of claim 1, in which the information transmitted by the at least one miniature electronic circuit is mediated by reflection of electromagnetic radiation.

5. The apparatus of claim 1, in which the information transmitted by the at least one miniature electronic circuit is mediated by emanation of sonic or ultrasonic energy.

6. The apparatus of claim 1, in which the information transmitted by the at least one miniature electronic circuit is mediated by reflection of sonic or ultrasonic energy.

7. The apparatus of claim 1, in which the information transmitted by the at least one miniature electronic circuit is mediated by quantum entanglement.

8. The apparatus of claim 2, in which the magneto-electric sensor is sensitive to voltage.

9. The apparatus of claim 2, in which the magneto-electric sensor is sensitive to electrical current.

10. The apparatus of claim 1, in which the miniature electronic circuit is powered by an external electromagnetic field generated by the generator of spatially-variant magnetic gradient located at least in part external to the subject's body.

11. The apparatus of claim 1, in which the miniature electronic circuit is powered by ultrasound waves in the subject's body.

12. The apparatus of claim 1, in which the miniature electronic circuit is powered by at least one chemical in its surroundings.

13. The apparatus of claim 12, wherein the chemical is glucose.

14. A method for imaging a portion of a subject's brain, the method comprising:

introducing at least one miniature electronic circuit that is less than 10 microns in size of a smallest dimension into the subject's brain, the at least one miniature electronic circuit including a magneto-electric sensor that senses magnetic fields and encodes a magnitude and/or direction of the sensed magnetic fields and a transmitter of information from the miniature electronic circuit;

generating at least one spatially-variant magnetic gradient using a generator that is positioned at least in part external to the subject's body, wherein the at least one miniature electronic circuit sensor detects current generated in neurons in the subject's brain;

transmitting information to an external receiver in a manner that depends on the current or voltage detected by the magneto-electric sensor included in the at least one miniature electronic circuit; and receiving the information transmitted by the transmitter of radiation at a receiver located at least in part external to the subject's body.

15. The method of claim 14, wherein the magneto-electric sensor is within or otherwise attached to the at least one miniature electronic circuit, wherein output of the magneto-electric sensor is used by the at least one miniature electronic circuit to modulate information emitted by the at least one miniature electronic circuit.

16. The method of claim 14, in which the information transmitted by the at least one miniature electronic circuit is mediated by emanation of electromagnetic radiation.

17. The method of claim 14, in which the information transmitted by the at least one miniature electronic circuit is mediated by reflection of electromagnetic radiation.

18. The method of claim 14, in which the information transmitted by the at least one miniature electronic circuit is mediated by emanation of sonic or ultrasonic energy.

19. The method of claim 14, in which the information transmitted by the at least one miniature electronic circuit is mediated by reflection of sonic or ultrasonic energy.

20. The method of claim 14, in which the information transmitted by the at least one miniature electronic circuit is mediated by quantum entanglement.

21. The method of claim 15, in which the magneto-electric sensor is sensitive to voltage.

22. The method of claim 15, in which the magneto-electric sensor is sensitive to electrical current.

23. The method of claim 14, in which the miniature electronic circuit is powered by an external electromagnetic field generated by the generator of spatially-variant magnetic gradient located at least in part external to the subject's body.

24. The method of claim 14, in which the miniature electronic circuit is powered by ultrasound waves in the subject's body.

25. The method of claim 14, in which the miniature electronic circuit is powered by at least one chemical in its surroundings.

26. The method of claim 25, wherein the chemical is glucose.

27. The apparatus of claim 1, further comprising a plurality of miniature electronic circuits located in the body or body part including the at least one miniature electronic circuit, wherein each of the plurality of miniature electronic circuits are less than 10 microns in size of a smallest dimension, wherein each of the plurality of miniature electronic circuits includes a magneto-electric sensor that senses magnetic fields and a transmitter of information from that particular miniature electronic circuit, wherein each of the plurality of miniature electronic circuits transmit information to the external receiver in a manner that depends on the current or voltage detected by the magneto-electric sensor included in each of the plurality of miniature electronic circuits, and wherein the information transmitted by the transmitters of at least two of the plurality of miniature electronic circuits is received at the receiver located at least in part external to the subject's body.

28. The apparatus of claim 27, wherein the information transmitted to the receiver includes position information from the at least two of the plurality of miniature electronic circuits.

29. The method of claim 14, wherein the method further comprises the introduction of a plurality of miniature electronic circuits that are less than 10 microns in size of a smallest dimension into the subject's brain,
- wherein each of the plurality of miniature electronic circuits includes a magnet-electric sensor that senses magnetic fields and encodes a magnitude and/or direction of the sensed magnetic fields and a transmitter of information from that particular miniature electronic circuit,
- wherein each of the plurality of miniature electronic circuits transmit information to the external receiver in a manner that depends on a current or voltage detected by the magneto-electric sensor included in each of the plurality of miniature electronic circuits, and
- wherein the information transmitted by the transmitters of at least two of the plurality of miniature electronic circuits is received at the receiver located at least in part external to the subject's body.

30. The method of claim 29, wherein the information transmitted to the receiver includes position information from the at least two of the plurality of miniature electronic circuits.

\* \* \* \* \*